United States Patent [19]
White

[11] 4,100,626
[45] Jul. 18, 1978

[54] WRIST IMPLANT APPARATUS

[75] Inventor: Robert Charles White, Beamsville, Canada

[73] Assignee: Ontario Research Foundation, Mississauga, Canada

[21] Appl. No.: 792,124

[22] Filed: Apr. 29, 1977

[51] Int. Cl.² ............................................. A61F 1/24
[52] U.S. Cl. ................................... 3/1.91; 128/92 C; 128/92 E; 128/92 EC
[58] Field of Search .................. 3/1.91, 1.9, 1.911, 3/1; 128/92 C, 92 E, 92 EC

[56] References Cited
U.S. PATENT DOCUMENTS

| | | | |
|---|---|---|---|
| 2,562,419 | 7/1951 | Ferris | 128/92 E |
| 3,837,008 | 9/1974 | Bahler et al. | 3/1.91 |
| 3,867,932 | 2/1975 | Huene | 128/92 E |
| 4,003,096 | 1/1977 | Frey | 3/1.91 |
| 4,040,130 | 8/1977 | Laure | 3/1.91 |
| 4,063,314 | 12/1977 | Loda | 3/1.91 |

Primary Examiner—Ronald L. Frinks
Attorney, Agent, or Firm—Sim & McBurney

[57] ABSTRACT

This invention provides a wrist implant as part of an apparatus including tools for assembly and disassembly of the implant. The implant includes a radial component adapted for insertion in the radius, the radial component supporting a pin member with a waisted central location, a ring of low-friction material with a part-spherical outer surface and a central passageway complementary with the pin member so that it can be snap-fitted thereover, and a metacarpal component adapted to be inserted in the third metacarpal and defining a receiving portion which has a part-spherical cavity adapted to receive the ring snugly but rotatably.

6 Claims, 5 Drawing Figures

WRIST IMPLANT APPARATUS

This invention relates generally to the surgical restructuring of joints in the body, and has to do particularly with a wrist implant adapted for use when the carpus or wrist has become damaged either through accident or degenerative disease.

When the wrist joint becomes deteriorated, either through degenerative disease or through accidents which cause damage or destruction to the bones, it is often possible to provide the patient with limited wrist movement by implanting a mechanical joint defining a pivot point for the carpus and hand with respect to the forearm bones. Typically, the prior art provides implant devices which include a metacarpal component having a rod or probe adapted to be inserted axially in the third metacarpal bone, and a radial component with a probe adapted to be inserted axially into the end of the radius in the forearm. However, prior art devices heretofore developed, while providing for some degree of movement of the wrist with respect to the forearm, have not allowed sufficient strength at the pivot location to prevent dislocation mediolaterally or sublaxation when the joint is greatly stressed as during a fall or a sudden impact against the hand.

It is an aspect of this invention to provide a wrist implant device which allows a large degree of rotational, mediolateral and flexural freedom to the patient, while at the same time providing a firm universal pivot point which is capable of withstanding a large degree of shock and suddenly applied stress without dislocation.

Accordingly, this invention provides a wrist implant apparatus, comprising:

a radial component having an elongated portion for insertion into the radius, a support portion integral with one end of the elongated portion, and a pin member integral with and supported by the support portion, the pin member being centrally waisted and having its axis substantially at right angles to the elongated portion, a ring of low-friction material, the ring having a part-spherical outer surface and a central passageway shaped to be complementary with and to receive the pin member, and a metacarpal component having an elongated portion for insertion into a metacarpal bone, and a receiving portion defining a part-spherical cavity adapted to receive the ring snugly but rotatably.

One embodiment of this apparatus is illustrated in the accompanying drawings, in which like numerals denote like parts throughout the several views, and in which.

Figure 1:
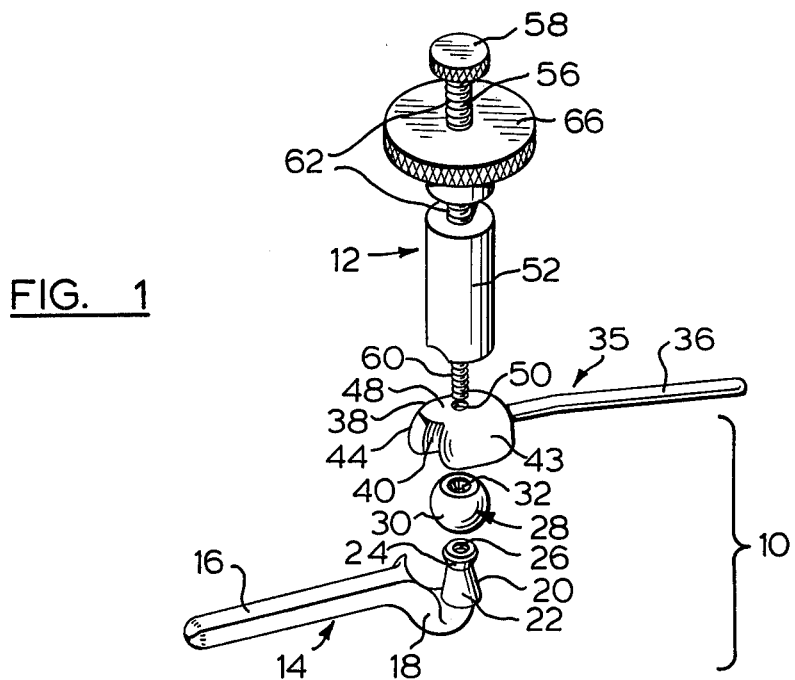
FIG. 1 is an exploded view of the components of the implant and an assembly tool used to assemble the implant after the individual components have been inserted into the respective bones of the forearm and hand.

Attention is first directed to FIG. 1 in which the components within the bracket 10 are those of the implant proper, and in which an assembly tool 12 is also illustrated.

Figure 2:
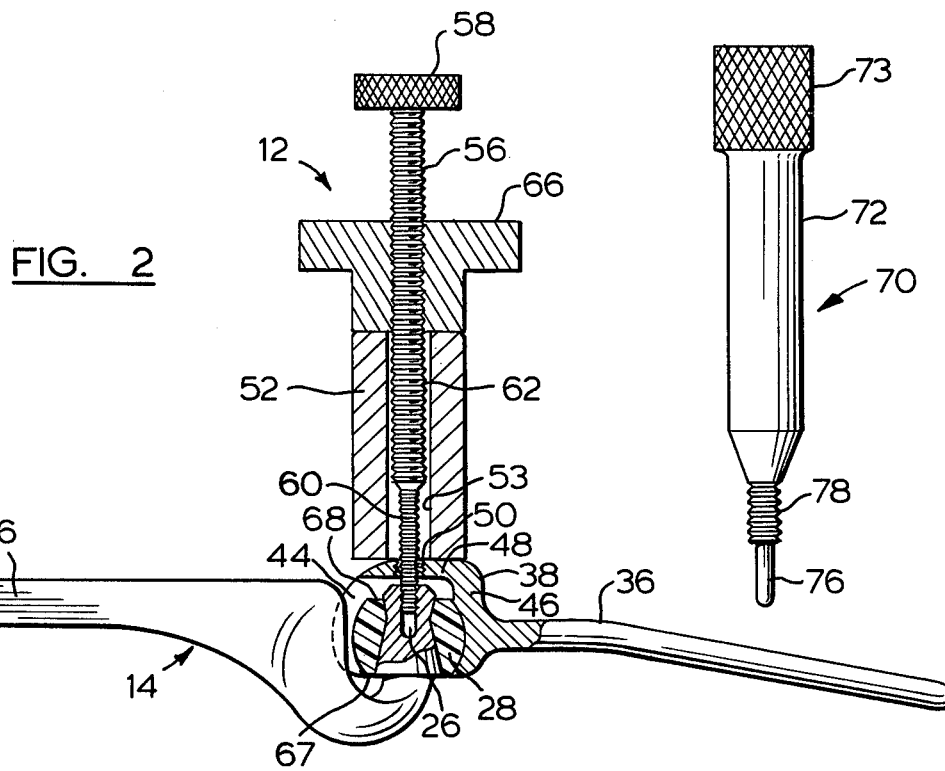
FIG. 2 is an elevational view, partly in section, of the components of FIG. 1 just after completed assembly, and also shows in elevation a disassembly tool.
Figure 5:
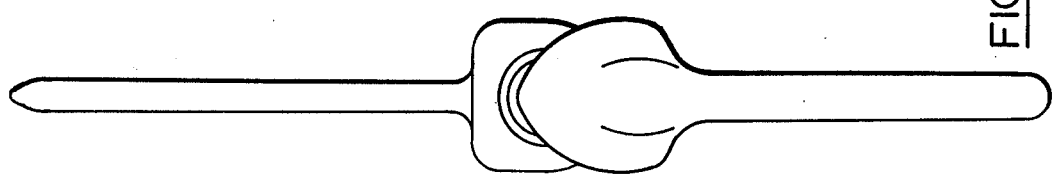
FIG. 5 is a palmar view (i.e. from underneath) of the components shown in FIG. 3.

The implant 10 includes a radial component 14 which has an elongated portion 16 for insertion into the radius bone in the forearm, a support portion 18 integral with the rightward end of the elongated portion 16, and a pin member 20 integral with and supported by the support portion 18. The pin member 20 defines a first frustoconical surface 22 and a second frusto-conical surface 24. The frusto-conical surface 24 has a smaller axial length than the frusto-conical surface 22, and as can be seen the two surfaces 22 and 24 converge toward each other. The pin member 20 has a blind, axial, tapped bore 26 extending down from the top thereof, for a purpose which will presently be explained. As can be seen in FIGS. 1 and 2, the pin member 20 has its axis substantially at right angles to the elongated portion 14.

The wrist implant 10 further includes a ring 28 of low-friction material, for example, of ultra high molecular weight polyethylene (medical grade polyethylene) which has a part-spherical outer surface 30 and a central passageway 32 shaped to be complementary with and to receive snugly the pin member 20. Because of the waisted region of the pin member 20 where the two frusto-conical surfaces 22 and 24 meet, the ring 28 must be snap-fitted over the pin 20. This snap-fitting is accomplished with the use of the tool 12, and will be described in detail subsequently.

The wrist implant 10 further includes a metacarpal component 35 which has an elongated portion 36 for insertion into a metacarpal bone (usually the third metacarpal), and a receiving portion 38 which defines a part-spherical cavity 40 adapted to receive the ring 28 snugly but rotatably.

Figure 4:
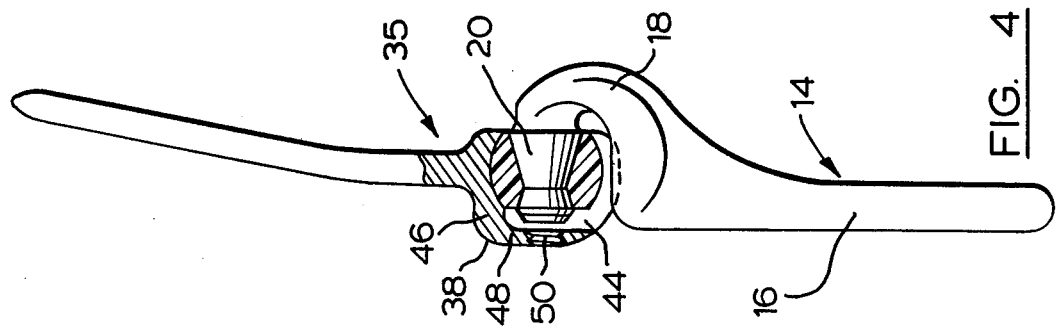
FIG. 4 is a partly sectioned elevational view of the components of FIG. 3.
Figure 3:
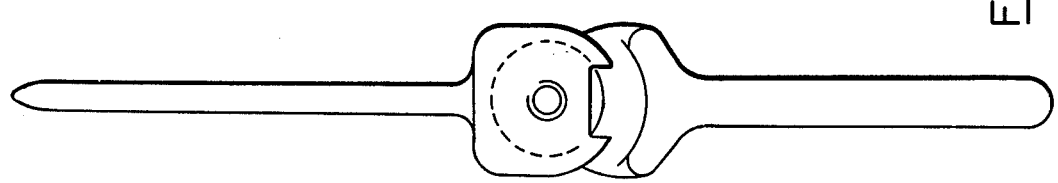
FIG. 3 is a dorsal view of the wrist implant with the appropriate portions for lodging in the bones.

As best seen with the help of FIGS. 1, 2 and 4, the receiving portion 38 of the metacarpal component 35 is substantially shovel-shaped and defines two side walls 43 and 44, a rear wall 46 and a top wall 48 which bridges across between the side walls 43 and 44. The side and rear walls have their inner surfaces merging to define the part-spherical cavity 40 described earlier.

The top wall 48 of the receiving portion 38 has a threaded opening 50 through it in alignment with the center of curvature of the part-spherical cavity 40. It is important to note that the thread diameter of the blind, axial, tapped bore 26 in the pin member 20 has a thread diameter smaller than the thread root diameter of the threaded opening 50, such that a threaded shaft can engage the tapped bore 26 while slipping axially through the threaded opening 50.

The reason for this requirement will now become clear when studying the operation of the assembly tool 12 which is to be described. The assembly tool 12 includes a sleeve member 52 with a central bore 53, a threaded shaft 56 with a knob 58 at one end constituting means for rotating the shaft, a threaded region 60 at the other end for threaded engagement with the tapped bore 26, and an intermediate region 62 between the threaded region 60 and the knob 58. The intermediate region 62 is also threaded, and has an outside diameter sized to slip within the central bore 53 of the sleeve member 52. The assembly tool 12 further includes a knob 66 having a central tapped bore engaged with the threads of the intermediate region 62 of the threaded shaft 56.

When the radial component 14, the ring 28 and the metacarpal component 35 are to be assembled together, the ring 28 is firstly inserted into the part-spherical cavity 40 of the receiving portion 38 of the metacarpal component 35. This can be accomplished because the ring 28 is not a completed sphere, but rather it is shaped as a sphere with antipodal portions removed along parallel planes. This is best seen in FIG. 2, with the planes being represented by the lines 67 and 68. The central passageway 32 of the ring 28 has its axis normal to the planes 67 and 68. The distance between the planes 67 and 68 is such that the ring 28 can be turned edgewise, as it were, and slipped between the side walls 43 and 44 of the receiving portion 38 of the metacarpal component 35, and once in registry with the spherical cavity 40, can be rotated within the same to bring the central passageway 32 into axial alignment with the threaded opening 50.

The radial component 14 is then brought up against the ring 28 with the pin member 20 partly inserted into the central passageway 32 of the ring 28. Simple hand pressure will not be sufficient to pop the pin member 20 into the ring 28, because of the resilience of the material from which the ring member 28 is manufactured, and due to the waisted portion of the pin member 20 between the two frusto-conical surfaces 22 and 24.

With the components of the wrist implant 10 in the position just described, the tool 12 is brought into the position illustrated in FIG. 1, and with the knob 66 "backed off" to allow the sleeve member 52 to slide upwardly along the portion 62, the threaded region 60 at the lower end of the threaded shaft 56 is passed through the threaded opening 50 in the top wall 48 and is threaded into the tapped bore 26 in the pin member 20. The condition of the components will then be that which is shown in FIG. 2. In this position, the knob 66 is then rotated in the clockwise direction as seen from above to bring pressure downwardly against the sleeve member 52, which in turn, bears downwardly against the top wall 48 of the receiving portion 38, and literally forces the ring 28 down over the pin member 20 in a snap-fitting operation.

Once the components of the wrist implant 10 are assembled in the fashion just described, the knob 58 is rotated in the counter-clockwise direction to unscrew the threaded portion 60 from the pin member 20, and the tool 12 is then removed.

It will be understood that it is important for surgical reasons to be able to assemble the components of the wrist implant 10 together within the wound in the wrist of the patient from one side only, because of the tissues, muscles, tendons and bones which will be surrounding the implant on all sides but one. Typically, a wrist implant of this kind must be inserted surgically from the dorsal or upper side of the wrist, becuase too many important parts would have to be cut to allow the surgeon to enter from the palmar or underside of the wrist. The tool 12 is thus seen to be ideally suited for assembling the components of the wrist implant 10 from one side (the top or dorsal side) only.

If for any reason it is desired to disassemble the components while in the wrist of the patient, for example if complications have resulted and the implant must be removed and/or replaced, a disassembly tool 70 is provided, as illustrated in FIG. 2. The disassembly tool 70 includes a shaft 72 having a knurled knob 73 at one end comprising means for rotating the shaft, a pin portion 76 at the other end adapted to enter slidingly the tapped bore 26 in the pin member 20 and to bear against the blind lower end thereof, and a threaded portion 78 adjacent the pin portion 76, the threaded portion 78 being adapted to engage the threaded opening 50 in the top wall 48 of the receiving portion 38 of the metacarpal component 35.

Looking at FIG. 2, if it were imagined that the tool 70 were inserted in place of the tool 12 with the pin 76 seating at the bottom of the threaded bore 26 and the threaded portion 78 engaged with the threads of the opening 50, it will be understood that rotation in the clockwise sense (seen from above) of the tool 70 will force the pin member 20 downwardly away from the top wall 48, and will "snap" open the tight fit between the ring 28 and the pin member 20.

What I claim is:

1. A wrist implant apparatus comprising:
    a radial component having an elongated portion for insertion into the radius,
    a support portion integral with one end of the elongated portion, and a pin member integral with and supported by the support portion, the pin member being centrally waisted and having its axis substantially at right angles to the said elongated portion,
    a ring of low-friction material, the ring having a part-spherical outer surface and a central passageway shaped to be complementary with and to receive said pin member, and
    a metacarpal component having an elongated portion for insertion into a metacarpal bone, and a receiving portion defining a part-spherical cavity adapted to receive said ring snugly but rotatably.

2. The invention claimed in claim 1, in which the receiving portion of the metacarpal component is shovel-shaped and defines two side walls, a rear wall and a top wall bridging across the side walls, the side and rear walls having their inner surfaces merging to define said part-spherical cavity.

3. The invention claimed in claim 2, in which the said top wall has a threaded opening through it in alignment with the center of curvature of said part-spherical surface, the said pin member having a blind, axial, tapped bore of thread diameter smaller than the thread root diameter of said threaded opening in the top wall such that a threaded shaft can engage said tapped bore while slipping axially through said threaded opening.

4. The invention claimed in claim 3, which further includes an assembly tool comprising a sleeve member with a central bore, a threaded shaft with means for rotating the shaft at one end, a threaded region at the other end for threaded engagement with said tapped bore, and an intermediate region between the threaded region and the said means for rotating, the intermediate region being threaded and having an outside diameter sized to slip within the said central bore of the sleeve member, and a knob with a central tapped bore engaged with the threads of said intermediate region, whereby when the radial component, the ring and the metacarpal component are to be assembled together, the threaded region of the shaft can be passed through said threaded opening and screwed into said tapped bore while the sleeve member is located on the shaft between the knob and the metacarpal component, and the knob can be screwed along said intermediate region to urge the sleeve and the metacarpal component toward the radial component.

5. The invention claimed in claim 3, which further includes a disassembly tool comprising a shaft having means at one end for rotating the shaft, a pin portion at the other end adapted to enter slidingly said tapped bore and to bear against the blind end thereof, and a threaded portion adjacent the pin portion which is adapted to engage said threaded opening in the top wall of the receiving portion of the metacarpal component.

6. The invention claimed in claim 1, in which the pin member defines first and second frusto-conical surfaces axially aligned and converging toward each other, the surface adjacent the support portion being longer axially than the other surface and having a larger base diameter.

* * * * *